(12) United States Patent
Roessl

(10) Patent No.: US 11,043,313 B2
(45) Date of Patent: Jun. 22, 2021

(54) DEVICE AND METHOD FOR PHASE STEPPING IN PHASE CONTRAST IMAGE ACQUISITION

(71) Applicant: KONINKLIJKE PHILIPS N.V., Eindhoven (NL)

(72) Inventor: Ewald Roessl, Ellerau (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 16/622,321

(22) PCT Filed: Aug. 22, 2018

(86) PCT No.: PCT/EP2018/072697
§ 371 (c)(1),
(2) Date: Dec. 13, 2019

(87) PCT Pub. No.: WO2019/038342
PCT Pub. Date: Feb. 28, 2019

(65) Prior Publication Data
US 2020/0383651 A1 Dec. 10, 2020

(30) Foreign Application Priority Data
Aug. 23, 2017 (EP) .................................. 17187471

(51) Int. Cl.
*G01N 23/041* (2018.01)
*G21K 1/02* (2006.01)
(Continued)

(52) U.S. Cl.
CPC ............ *G21K 1/025* (2013.01); *A61B 6/4291* (2013.01); *G01N 23/041* (2018.02); *G21K 1/06* (2013.01);
(Continued)

(58) Field of Classification Search
CPC ....... G01N 23/20025; G01N 23/20075; G01N 2223/3303; G01N 2223/3307;
(Continued)

(56) References Cited

U.S. PATENT DOCUMENTS 9,179,883 B2 11/2015 Spahn
10,172,580 B2 1/2019 Daerr
(Continued)

FOREIGN PATENT DOCUMENTS

CN 101881601 A 11/2010
CN 206421821 U 8/2017
(Continued)

OTHER PUBLICATIONS

PCT International Search Report, International application No. PCT/EP2018/072697, dated Dec. 12, 2018.

*Primary Examiner* — Don K Wong
(74) *Attorney, Agent, or Firm* — Larry Liberchuk

(57) ABSTRACT

The present invention relates to a device for phase stepping in phase contrast image acquisition, the device (1) comprising: a mobile grating (10); a guiding element (11); a restoring element (12); and a locking element (13); wherein the guiding element (11) is configured to guide the mobile grating (10) between a first position (2) and a second position (3); wherein the restoring element (12) is configured to apply a force to the mobile grating (10); wherein the force is directed from the first position (2) to the second position (3); and wherein the locking element (13) is configured to releasably lock the mobile grating (10) in the first position (2). In an example, during the motion of the mobile grating (10) back to equilibrium, a decoder (11a) for the position of the mobile grating (10) along the guiding element (11) may trigger at least four measurement frames over a period of at least 2*Pi. The invention provides a device (1) for phase stepping in phase contrast image acquisition which (Continued)

provides a fast image acquisition without a significant delay and which reduces positional inaccuracies and which avoids back-lash.

11 Claims, 6 Drawing Sheets

(51) Int. Cl.
 *A61B 6/00* (2006.01)
 *G21K 1/06* (2006.01)
(52) U.S. Cl.
 CPC .......... *A61B 6/484* (2013.01); *G01N 2223/32* (2013.01); *G21K 2201/067* (2013.01); *G21K 2207/005* (2013.01)
(58) Field of Classification Search
 CPC .............. G01N 23/041; G01N 2223/32; A61B 6/5258; A61B 6/484; A61B 6/4035
 See application file for complete search history.

(56) References Cited

U.S. PATENT DOCUMENTS

| | | |
|---|---|---|
| 2007/0183562 A1 | 8/2007 | Popescu |
| 2007/0183583 A1 | 8/2007 | Baumann |
| 2010/0220834 A1 | 9/2010 | Heismann |
| 2012/0099702 A1 | 4/2012 | Engel |
| 2012/0114098 A1 | 5/2012 | Mikami |
| 2015/0030126 A1 | 1/2015 | Radicke |
| 2015/0294749 A1 | 10/2015 | Gorelick |
| 2016/0374635 A1 | 12/2016 | Ning |
| 2017/0082559 A1 | 3/2017 | Arboleda |
| 2019/0343472 A1* | 11/2019 | Sano ..................... A61B 6/00 |
| 2020/0158662 A1* | 5/2020 | Horiba ................ A61B 6/4291 |

FOREIGN PATENT DOCUMENTS

| | | |
|---|---|---|
| DE | 202016006600 U1 | 11/2016 |
| DE | 102016219158 A1 | 8/2017 |
| JP | H104531 A | 2/1998 |
| JP | H1048531 A | 2/1998 |
| JP | 2012065840 A | 4/2012 |
| JP | 2012115621 A | 6/2012 |
| WO | 2013004574 A1 | 1/2013 |
| WO | WO2015090949 A1 | 6/2015 |
| WO | WO2016075140 A1 | 5/2016 |

* cited by examiner

DEVICE AND METHOD FOR PHASE STEPPING IN PHASE CONTRAST IMAGE ACQUISITION

FIELD OF THE INVENTION

The present invention relates to a device and a method for phase stepping in phase contrast image acquisition.

BACKGROUND OF THE INVENTION

Phase stepping is a necessity in most of currently existing differential phase contrast setups making use of Talbot-Lau interferometry. The stepping is typically implemented by an actuator which activates any of the three gratings of a Talbot-Lau interferometer with respect to the two others in synchrony with the readout of the X-ray detector sensing the changes in intensity at various locations within the field-of-view induced by the stepping.

The activation leads to a positional shift of the grating. After the shifting of the grating the X-ray detector is read out. Therefore, the operator acquires a readout prior to the shifting and after the shifting. A further example is described in US 2015/0294749 A1 showing an interferometric dynamic-grating imaging method, a diffraction grating and an imaging apparatus. The interferometric dynamic grating is actuated by a microelectromechanical system (MEMS) to change its periodicity. A movable part of the dynamic grating is anchored by springs on two lateral sides of the grating in the direction of movement of the grating. Comb drive means on the sides of the grating allow for modification of the grating in the desired direction. The comb drive means may be piezoelectrically or electrostatically driven.

Known disadvantages of the above device include possible delays which are required before the X-ray readout of each phase step can be triggered in view of a possible time it takes the actuator to settle at the new position. Furthermore, positional inaccuracies, back-lash, etc. may occur.

SUMMARY OF THE INVENTION

There may thus be a need to provide a device for phase stepping in phase contrast image acquisition which provides a fast image acquisition without a significant delay and which reduces positional inaccuracies and which avoids back-lash.

The object of the present invention is solved by the subject-matter of the independent claims; further embodiments are incorporated in the dependent claims. It should be noted that the following described aspects of the invention apply also for the method.

According to the present invention, a device for phase stepping in phase contrast image acquisition comprises a mobile grating; a guiding element; a restoring element; and a locking element; wherein the guiding element is configured to guide the mobile grating between a first position and a second position; wherein the restoring element is configured to apply a force to the mobile grating; wherein the force is directed from the first position to the second position; and wherein the locking element is configured to releasably lock the mobile grating in the first position.

The mobile grating is mounted in a movable manner on the guiding element. When the mobile grating is in the first position, the restoring element applies a force to the mobile grating which directs the mobile grating towards the second position. Furthermore, a locking element may releasably lock the mobile grating in the first position. This means, that the mobile grating may be put into the first position and then be locked by the locking element. In the first position, the restoring element applies a force to the mobile grating which forces the mobile grating into the second position. Thus, after unlocking the locking element, i.e. releasing the mobile grating from the locking element, the restoring element forces the mobile grating towards the second position. The mobile grating and the restoring element may thus define a free oscillating system. This means, that the mobile grating may perform an oscillating movement along the guiding element.

Since the mobile grating performs the free movement along the guiding element, the invention does not need an actuator for performing the phase stepping movement of the mobile grating. By moving the mobile grating with the restoring element only, the invention provides a fast image acquisition without a significant delay since a detector does not need to wait for the end of a positioning process of the mobile grating. Thus, in a first embodiment, a detector may immediately start the measurement after the mobile grating is released by from the locking element. In a second alternative embodiment, the detector may start the measurement after a delay time to avoid measurements during the release of the mobile grating.

The position of the mobile grating is dynamic but can be determined by considering the mass of the mobile grating and the force being applied by the restoring element. Furthermore, due to the known free movement of the mobile grating along the guiding element, positional inaccuracies are reduced and back-lash is avoided.

According to an example, the device comprises a position decoder, wherein the position decoder is configured to detect the position of the mobile grating along the guiding element and to emit a trigger signal for a detector if the mobile grating passes predefined positions along the guiding element.

The position decoder may track the position of the mobile grating during the oscillation process. Thus, the exact position of the mobile grating between the first and the second position is known. This ensures that the readout is triggered always at exactly the same locations and it will improve the reproducibility and accuracy of the data. The decoder signals will trigger the detector readout and could also trigger the X-ray tube emission in case the latter is not continuous.

In another example, the mobile grating performs the free oscillation starting from the first position towards the second position. The oscillation may be described by the equation of motion $$\ddot{x}(t) + 2\gamma \dot{x}(t) + \omega^2 x(t) = 0$$

with x being the linear position of the mobile grating, t the time, $\omega$ being the angular frequency with $\omega^2 = k/m$ with k being a spring constant and m being a spring mass, and $\gamma = d/2$ with d being the damping constant. In case of the free oscillation the damping constant is zero. A solution of the equation of motion for the free oscillation is given by $$x(t) = x_0 \cos \omega t.$$

In case of a damped oscillation, a solution of the equation of motion may be given by $$x(t) = e^{-\gamma t}\left(c_1 e^{\sqrt{\gamma^2-\omega^2}\,t} + c_2 e^{-\sqrt{\gamma^2-\omega^2}\,t}\right),$$

wherein $c_1$ and $c_2$ are complex constants being determined by the initial conditions.

According to an example, the force applied by the restoring element on the mobile grating reduces to zero when the mobile grating reaches the second position. The restoring element does not apply any force on the mobile grating in the second position. While the mobile grating leaves the second position, the restoring element restarts forcing the mobile grating towards the second position.

In another example, arriving in the second position, the mobile grating may advance into a third position in which the restoring element forces the mobile grating back towards the second position. Thereby, the second position is arranged between the first position and the third position. Therefore, the mobile grating may oscillate around the second position, wherein the first position and the third position define maxima of the oscillation.

In another example, the first position may be the maximum of a cosine or cosine-like movement wherein the second position may be the zero point of a cosine-like movement. The restoring element applies the maximum force to the mobile grating in the first position.

According to another example, the mobile grating is configured to perform a continuous movement between the first position and the second position.

According to another example, the device further comprises: a dampening element; wherein the dampening element is configured to dampen a movement of the mobile grating between the first position to the second position. In terms of the movement equation the dampening element provides a non-zero dampening constant d.

In another example, the mobile grating, the restoring element and the dampening element define a damped oscillator system.

In an example, the dampening element applies friction to the mobile grating. This means, that if the mobile grating moves along the guiding element, the dampening element applies a frictional force to the mobile grating decreasing the movement velocity.

According to an example, the dampening element provides a controllable dampening to the mobile grating.

In an example, the dampening element may underdamp, critically damp, or overdamp the movement of the grating. The dampening constant in the under dampening case is $0<\gamma<\omega$, in the critical dampening case the dampening constant is $\gamma=\omega$ and in the over dampening case the dampening constant is $\gamma>\omega$.

According to an example, the dampening element applies at least a critical dampening to the movement of the mobile grating. This means that the dampening element may perform a critical dampening and/or an over dampening.

According to an example, the device further comprises: a displacement unit; wherein the displacement unit is configured to move the mobile grating into the first position. In another example, the displacement unit may move the mobile grating from the second position into the first position.

In another example, the displacement unit may be used to start the phase stepping process by bringing the mobile grating into the first position. After the displacement unit has brought the mobile grating into the first position, the locking element may lock the mobile grating in the first position. The displacement unit applies a greater force on the mobile grating than the restoring element. Furthermore, the force of the displacement unit is directed in the opposite direction to the force being applied by the restoring element. In another embodiment, when attaching the displacement unit to the mobile grating the restoring element may detach from the mobile grating. When the mobile grating reaches the first position, the displacement unit may detach from the mobile grating after the locking element locks the mobile grating in the first position and the restoring unit may attach to the mobile grating.

According to the present invention, a system for phase stepping in phase contrast image acquisition comprises: a phase contrast image acquisition apparatus; and a device according to one of the preceding claims; wherein the phase contrast image acquisition apparatus comprises a radiation source; and at least one immobile grating; wherein the radiation source defines a start of an optical path extending to the at least one immobile grating and the mobile grating; wherein a movement of the mobile grating from the first position to the second position shifts the mobile grating relative to the at least one immobile grating.

The system provides an easy way for applying a phase stepping by moving the mobile grating in a free oscillatory movement in relation to the radiation source and the immobile grating. In one embodiment, the mobile grating has grating structures and may move perpendicular to those grating structures, i.e. the guiding element leads the mobile grating perpendicularly to the grating structures. In another embodiment, the mobile grating may move in a non-parallel manner to the grating structures, that means that at least one angle between the movement direction of the mobile grating and the grating structures direction is smaller than 90° but still has a perpendicular movement component.

In an example the phase contrast image acquisition apparatus comprises two immobile gratings.

According to another example, the phase contrast image acquisition apparatus comprises: a detector; wherein the detector comprises a photodiode array and a scintillator; wherein the photodiode array matches the scintillator; wherein the detector is arranged on an end of the optical path; and wherein the detector is configured to completely read out the photodiode array at least four times during the movement of the mobile grating between the first position and the second position.

In another example, the detector may be a 2D detector which directly converts X-ray radiation into measurement signals.

In another example, the detector is immobile in relation to the mobile grating.

In another example, at or shortly prior to a scan trigger, the mobile grating is released and undergoes free, damped or undamped, oscillations during which the interferometric phase relations are continuously changing in a well-defined manner.

The detector can therefore immediately start a measurement since the detector does not have to wait for a special position of the mobile grating. The oscillation time constants are then preferentially chosen in comparison to the frame duration in such a way that the phase relation does not vary appreciably during one frame time. The detector performs a plurality of measurements while the mobile grating moves from the first position to the second position.

According to the present invention, also a method for phase stepping in phase contrast image acquisition comprises the following steps: a) locking a mobile grating in a first position with a locking element, wherein the mobile grating is movable between the first position and a second position; b) applying a force on the mobile grating with a restoring element, wherein the force is directed from the first position to the second position; and c) unlocking the locking element such that the force moves the mobile grating into the second position; wherein step b) may be performed at the same time with and/or after step a).

According to an example, the method further comprises the step: d) reading out a detector on which X-ray radiation passing the mobile grating falls on.

In an example, the mobile grating and at least one immobile grating have different pitches.

In another example, the mobile grating has a larger pitch than the at least one immobile grating.

Furthermore, according to the present invention, a computer program element for controlling an apparatus according to the preceding description, which, when being executed by a processing unit, is adapted to perform the method steps being described above.

A computer readable medium having stored the program element of the preceding description. These and other aspects of the present invention will become apparent from and be elucidated regarding the embodiments described hereinafter.

BRIEF DESCRIPTION OF THE DRAWINGS

Exemplary embodiments of the invention will be described in the following regarding the following drawings.

DETAILED DESCRIPTION OF EMBODIMENTS

Figure 1A:
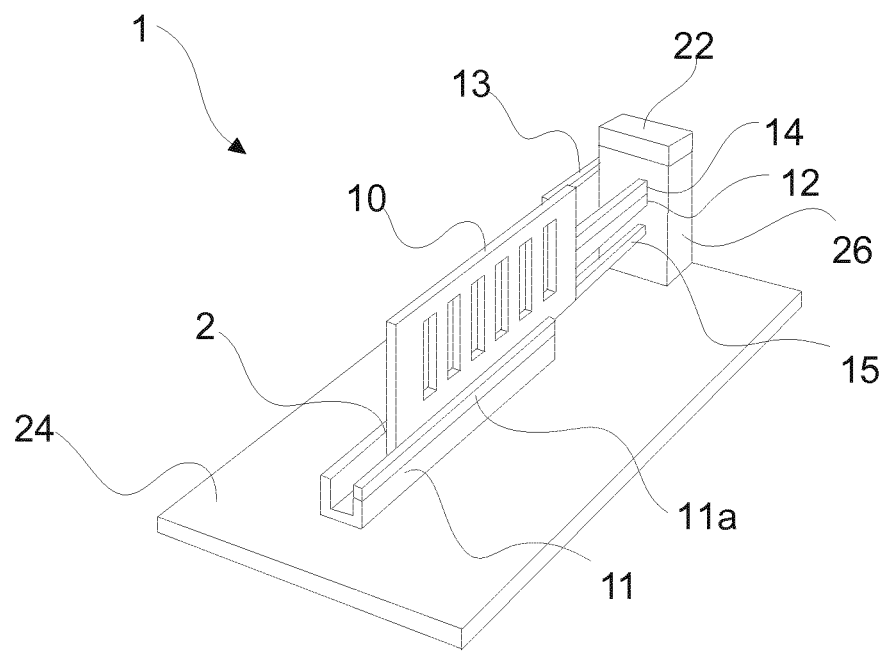
FIG. 1a-d show schematic drawings of the device with the mobile grating in different positions.

The device for phase stepping in phase contrast image acquisition is referenced in its entirety with reference number 1 as shown in FIG. 1a-d. The device 1 comprises a mobile grating 10, a guiding element 11, a restoring element 12, a locking element 13, a dampening element 14, and a displacement unit 15.

Figure 1B:
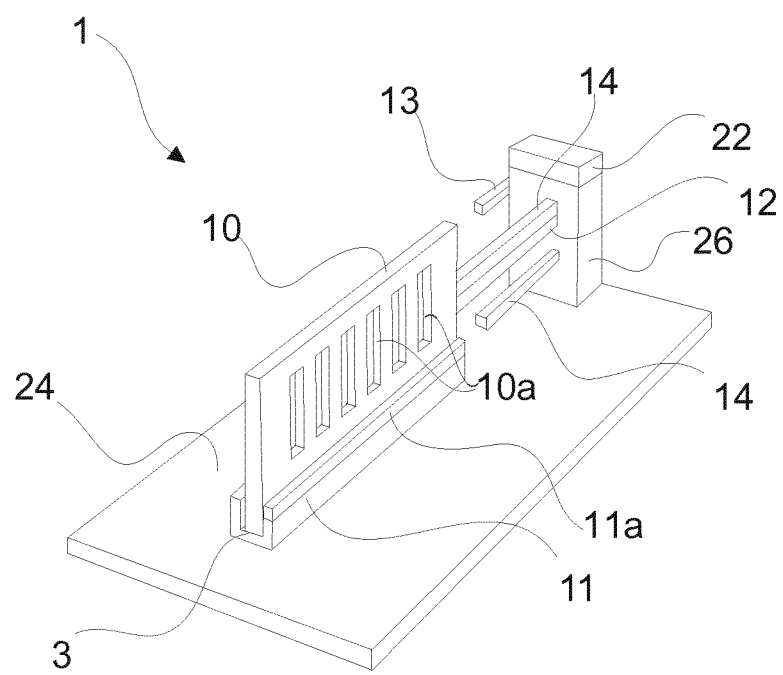
Figure 1C:
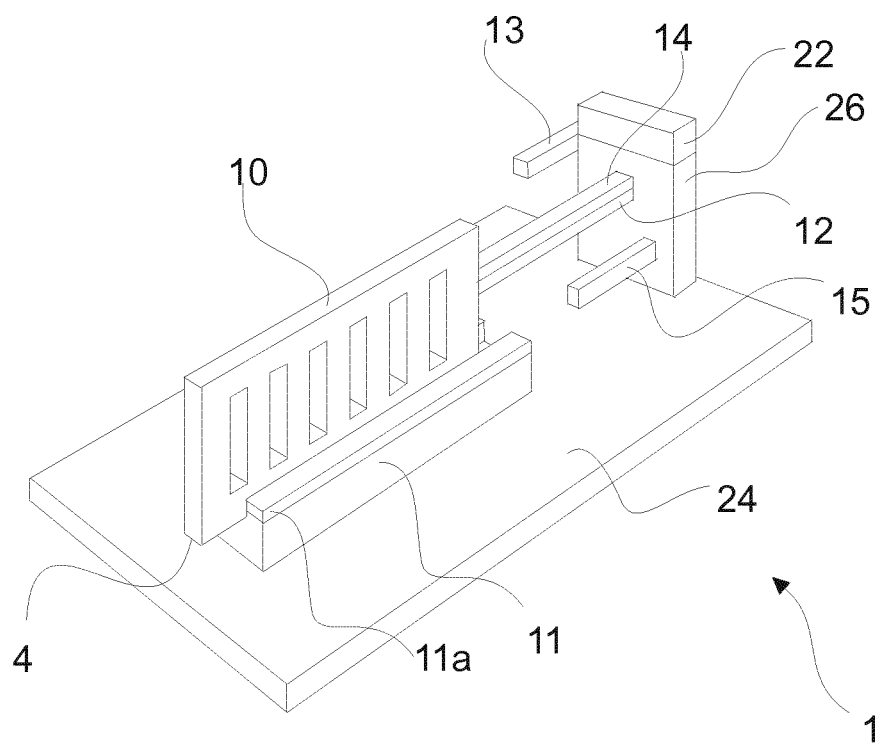

The mobile grating 10 is arranged on the guiding element 11 which guides the mobile grating 10 from a first position 2 shown in FIG. 1a to a second position 3 shown in FIG. 1b. In an exemplary embodiment, the guiding element 11 may be a guide rail along which the mobile grating 10 is guided. In another exemplary embodiment, the guiding element 11 may be a guide edge (not shown), along which the mobile grating 10 is guided from the first position 2 to the second position 3.

The restoring element 12 is attached to the mobile grating 10. The restoring element 12 may comprise a connection to an element 26 being immobile in relation to the mobile grating 10. In an exemplary embodiment, the restoring element 12 may be a mechanical spring. In another exemplary embodiment, the restoring element 12 may be an electrical or electromagnetic oscillating element or in a further exemplary embodiment a hydraulic oscillating element. The restoring element 12 applies a force to the mobile grating 10 when the mobile grating 10 is in the first position 2. The force which the restoring element 12 applies to the mobile grating 10 in the first position 2 is directed such, that the mobile grating 10 is moved into the second position 3.

In the second position 3, the restoring element 12 does not apply a force on the mobile grating 10. The force of restoring element 12 in the second position 3 is therefore zero. The force of the restoring element 12 on the mobile grating 10 decreases between the first position 2 and the second position 3. Thus, the restoring element 12 applies a restoring force to the mobile grating 10 if the mobile grating 10 is removed from the second position 3. Furthermore, the mobile grating 10 and the restoring element 12 define a free oscillating system. The only force which moves the mobile grating 10 results from the restoring element 12.

The distance between the first position 2 and the second position 3 spans at least the pitch of the mobile grating 10. Particularly, the distance may be several times this length. This enables covering at least the entire angular span from 0 to 2*Pi for the phase stepping.

Locking element 13 is configured to lock the position of the mobile grating 10 in the first position 2. This means that if the mobile grating 10 is in the first position 2, the locking element 13 may be actuated such that the mobile grating 10 cannot leave the first position 2, anymore. In this state, the restoring element 12 may still apply a force on the mobile grating 10 which is directed from the first position 2 to the second position 3. However, since the locking element 13 locks the mobile grating 10 in the first position 2, the mobile grating 10 will not move when being locked by the locking element 13.

The locking element 13 is configured to apply a releasable lock on the mobile grating 10. This means that the locking element 13 may be unlocked such that the mobile grating 10 is released from the locking element 13. If the locking element 13 releases the mobile grating 10, the force being applied by the restoring element 12 to the mobile grating 10 will move the mobile grating 10 from the first position 2 to the second position 3.

The locking element 13 is connected to an element which is immobile relative to the mobile grating 10. According to FIGS. 1a-d this may be element 26. If the mobile grating 10 comes into the first position 2, the locking element 13 may connect to the mobile grating 10 in a clamping or form fit manner. In an exemplary embodiment, the locking element 13 may e.g. comprise a pin which may connect to a corresponding recess on the mobile grating 10. In another exemplary embodiment, the locking element may comprise an electromagnet, wherein the mobile grating may comprise a permanent magnet. The locking is performed if the electromagnet is switched on and if the electromagnet and the permanent magnet are arranged next to each other.

In another exemplary embodiment (not shown), the locking element 13 may be arranged on the guiding element 11. In this case, the locking element 13 is rigidly connected to the guiding element 11 such that the locking element 13 does not move relative to the guiding element 11. The locking element 13 may then for example clamp the mobile grating 10. In another example, the locking element 13 may block the movement of the mobile grating 10 in a form-fit manner, e.g. the locking element 13 may block the mobile grating 10 on the guiding element 11.

Figure 1D:
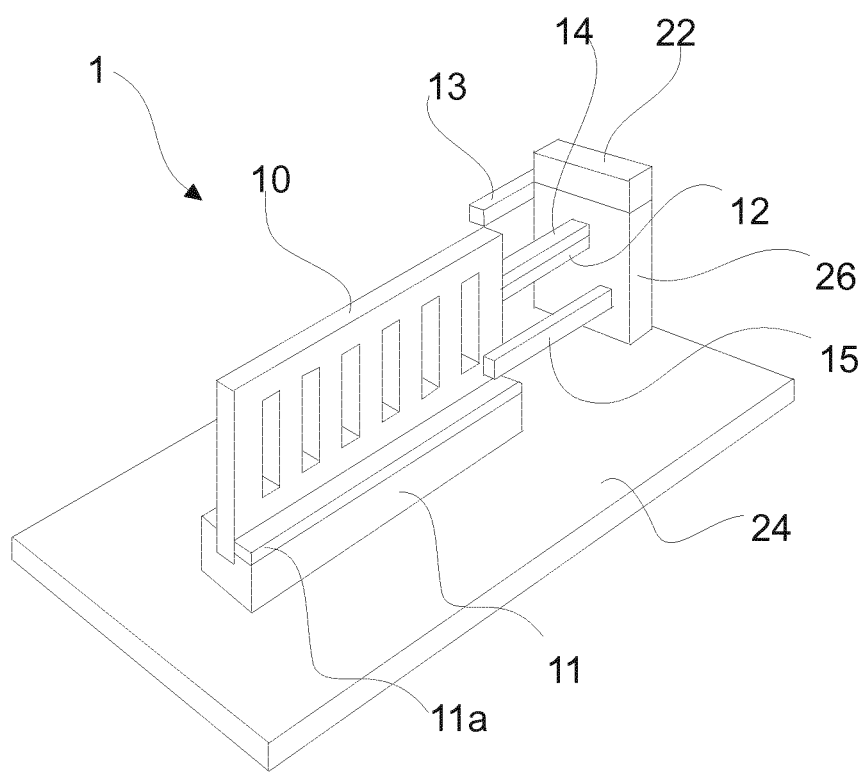

The dampening element 14 dampens the movement of the mobile grating 10 when moving along the guiding element 11. Thus, the combination of the mobile grating 10, the restoring element 12 and the dampening element 14 define a damped oscillating system. In an exemplary embodiment, the dampening element 14 may provide a force on the mobile grating 10 which is directed opposite to the force being applied by the restoring element 12 as shown in FIGS. 1a-d. In an example, the dampening element 14 may be integrated into the restoring element 12. In another exemplary embodiment, the dampening element 14 provides a friction force to the mobile grating 10 when the mobile grating 10 moves along the guiding element 11. Two further exemplary embodiments of the guiding element 11 are shown in FIGS. 2a and 2b.

In another exemplary embodiment (not shown), the dampening element 14 may be a permanent or electro magnet and the mobile grating may comprise a conductor or vice versa. The dampening then results from relative movement of the conductor and the magnet, since eddy currents are induced in the conductor.

The dampening being provided by the dampening element 14 may be chosen such that the phase sampling is as smooth and uniform as possible.

Figure 2A:
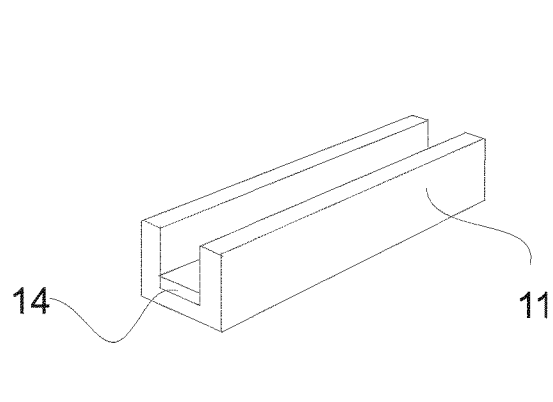
FIG. 2a, b shows schematic drawings of different embodiments of the guiding element.
Figure 2B:
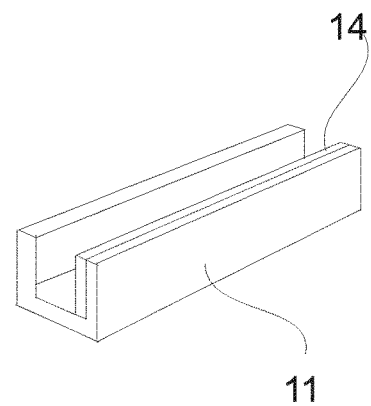

FIG. 2a shows a guiding element 11 being formed out as a guide rail. The dampening element 14 is positioned on the bottom of the guiding element 11. While gliding along the guide rail, the mobile grating 10 may contact the dampening element 14 which applies a friction force on the mobile grating 10.

In FIG. 2b, the dampening element 14 is positioned on an inner lateral side of the guiding element 11 which comes into contact with the mobile grating 10. While the mobile grating 10 moves along the guide rail, the dampening element 14 applies a force being directed opposite to the force being applied by the restoring element 12.

Concerning the damped oscillation of the mobile grating 10, if the dampening d provided by the dampening element 14 is zero, the movement of the mobile grating 10 will be a free oscillation.

Figure 4A:
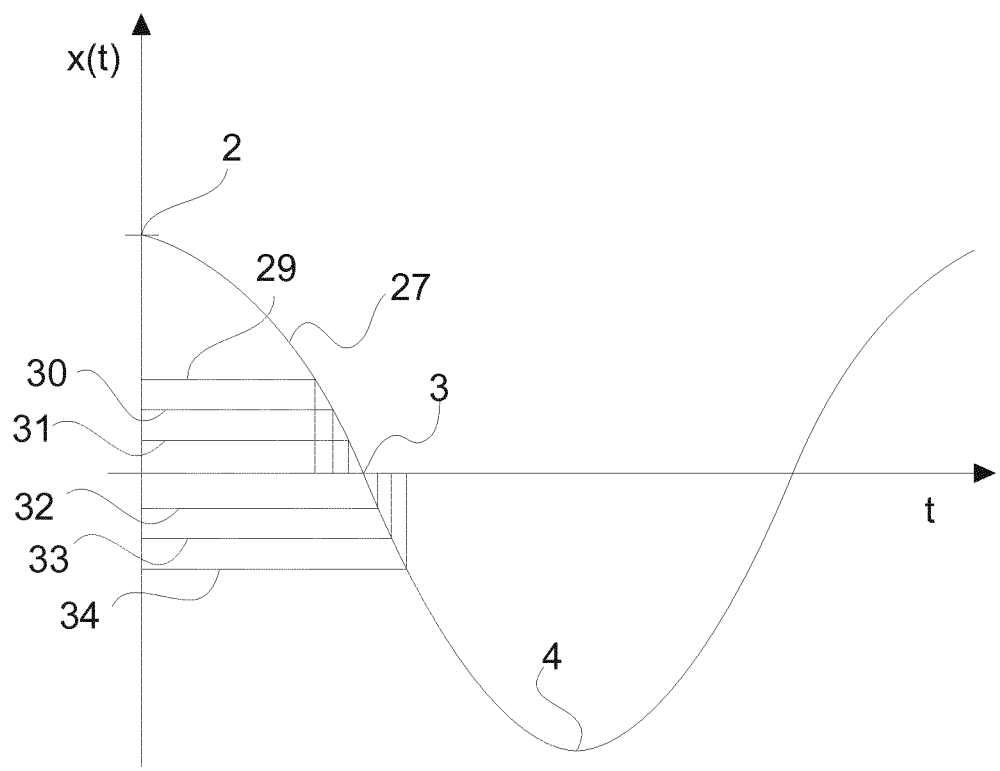
FIG. 4a-d show schematic diagrams of the undamped (a) and damped (b-d) movement of the mobile grating.

A diagram showing the movement of a free oscillating mobile grating 10 is shown in FIG. 4a. The movement of the mobile grating 10 in this case follows a cosine function 27. The starting point of the cosine function is at the first position 2. The movement of the mobile grating 10 then transfers the mobile grating 10 to the second position 3 and further into a third position 4.

A phase stepped measurement for the phase-contrast image acquisition may be applied in the linear portion of the cosine function 27 being indicated by the bars 29 to 34. In this portion, the cosine function 27 is close to a linear function.

Figure 4B:
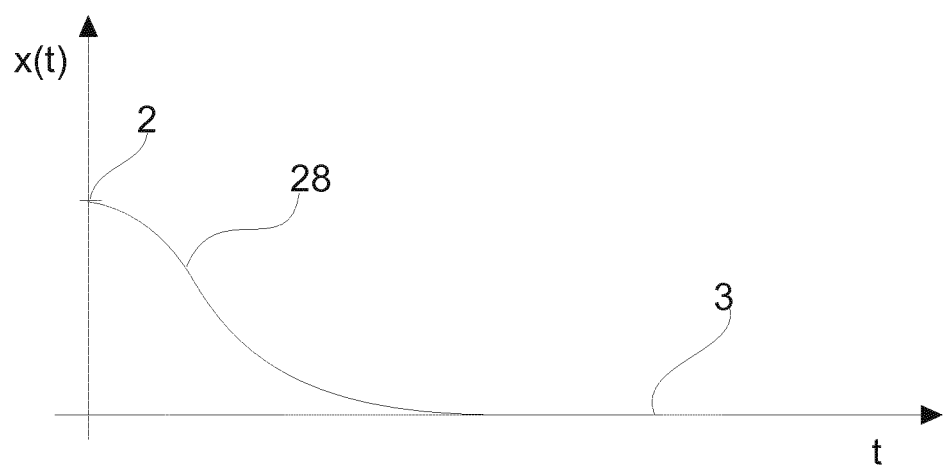

The dampening being provided by the dampening element 14 may further be under dampening, critical dampening or over dampening. In the free oscillating (FIG. 4a) and in the under dampening case being shown in FIG. 4d, the movement of the mobile grating 10 will transfer from the first position 2 to the second position 3 and then further towards or in direction of the third position 4 being shown in FIG. 1c. In the third position 4, the restoring element 12 applies a force to the mobile grating 10 which is directed to the second position 3. The mobile grating 10 will therefore oscillate around the second position 3.

In the under dampening case, the distance which the mobile grating 10 moves from the second position 3 will exponentially decrease with every passing of the second position 3 until the mobile grating 10 will stop its movement in the second position 3.

Figure 4C:
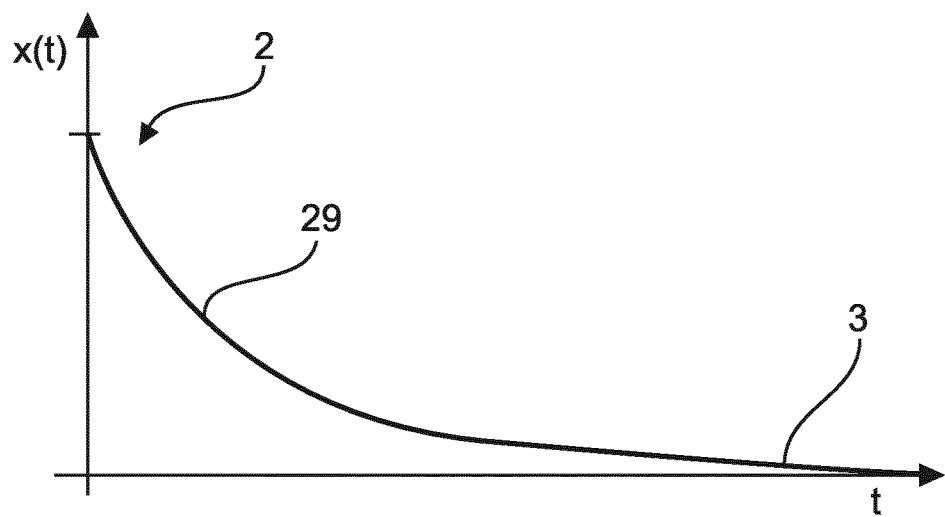
Figure 4D:
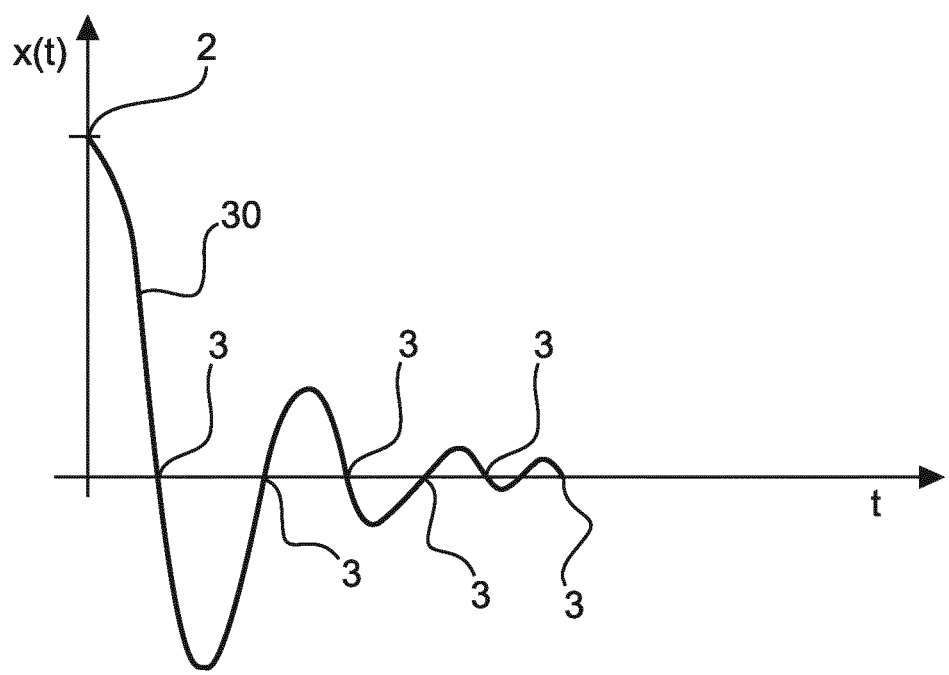

In the critically dampened case being shown in FIG. 4c, the mobile grating 10 will move from the first position 2 to the second position 3 and then stay in the second position 3. This means, that the mobile grating 10 will slow down with an exponential decay on the way to the second position 3 and then stop when reaching the second position 3.

In the over damped case, the mobile grating will move slower than in the critically damped case from the first position 2 to the second position 3 and then stop in the second position 3.

An example of an over damped case is shown in FIG. 4b. The movement path 28 starts at the first position 2 and then transfers towards the second position 3. When approaching the second position 3, the movement of the mobile grating 10 until it stops when the mobile grating 10 reaches the second position 3.

The displacement unit 15 displaces the mobile grating 10 from the second position 3 to the first position 2 when the mobile grating 10 has stopped in the second position 3. The beginning of the displacement of the mobile grating 10 by the displacement unit 15 is shown in FIG. 1d. The displacement unit 15 may apply a stronger force to the mobile grating 10 as the restoring element 12 wherein the force of the displacement unit 15 is directed opposite to the force of the restoring element 12. After the displacement unit 15 has brought the mobile grating 10 into the first position 2, the locking element 13 will lock the mobile grating 10 in the first position 2. After the locking element 13 locks the mobile grating, the displacement unit 15 stops applying force to the mobile grating 10. In an exemplary embodiment, the displacement unit 15 may be detached from the mobile grating 10 after the mobile grating 10 arrives the first position 2. In a further exemplary embodiment, the displacement unit 15 may be detached from the mobile grating 10 if the locking element 13 locks the mobile grating 10 in the first position 2.

In an exemplary embodiment, the components of the device 1 may be arranged on a base plate 24. However, they may also be arranged on further objects in further exemplary embodiments, as on a frame or the like.

Figure 3:
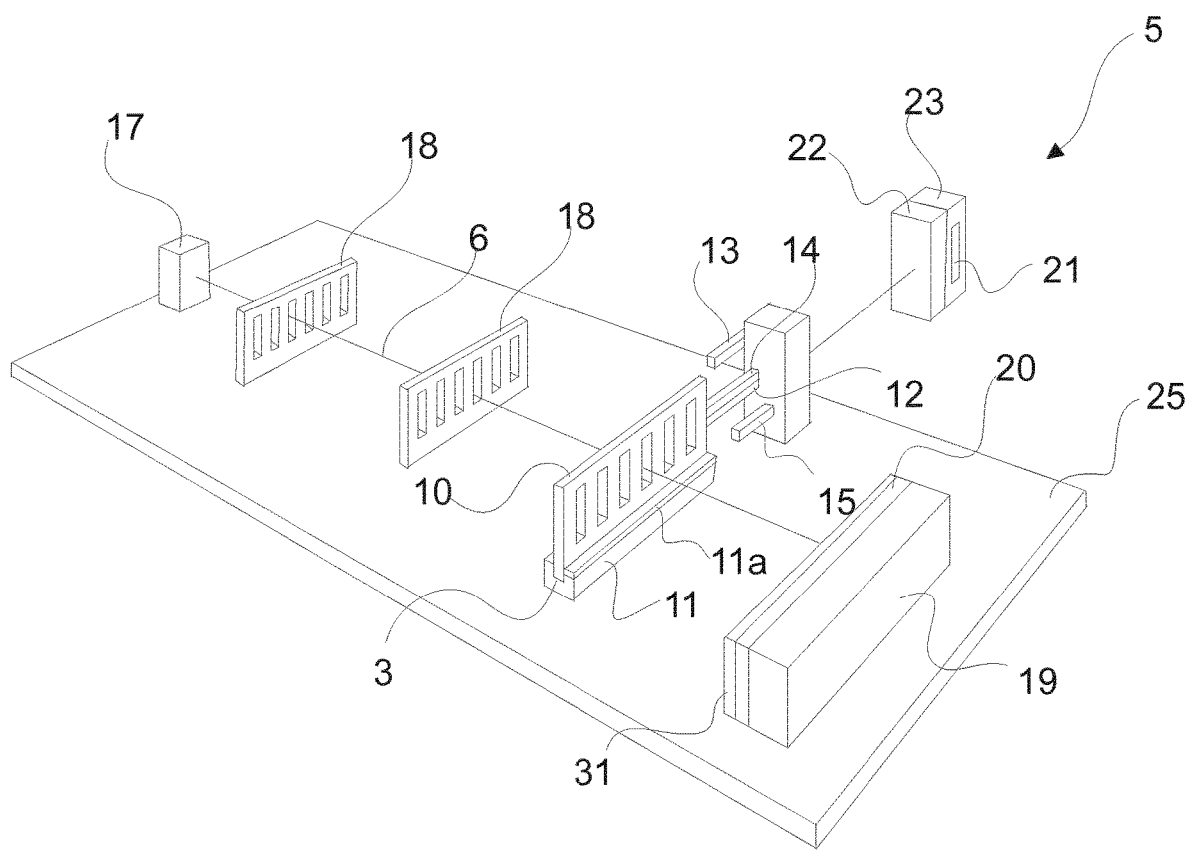
FIG. 3 shows a schematic drawing of the system.

Regarding FIG. 3, a system 5 for phase stepping in phase contrast image acquisition is described. The system 5 comprises a device 1 and a phase contrast image acquisition apparatus 16. The phase contrast image acquisition apparatus 16 comprises a radiation source 17, at least one immobile grating 18, a detector 19 comprising a photodiode array 20, a scintillator 20a, and a processing unit 22. The photodiode array 20 matches the scintillator 20a.

In an example, the phase contrast image acquisition apparatus 16 may be a mammography apparatus, diagnostic X-ray apparatus, an IGT apparatus, or a CT apparatus. Furthermore, the phase contrast image acquisition apparatus 16 may be used in material and/or food inspection as well as non-destructive testing or dental imaging. Therefore, the immobile grating 18 and the mobile grating 10 may be X-ray gratings and the radiation source 17 may be an X-ray radiation source.

The radiation source 17 defines a starting point for an optical path 6 which extends from the radiation source 17 to the detector 19. In an example, the optical path 6 is the interferometric optical path of a Talbot-Lau interferometer. The mobile grating 10 is one of the G0, G1, or G2 gratings wherein the remaining gratings are immobile gratings 18.

The immobile grating 18 and the mobile grating 10 of the device 1 are positioned along the optical path 6. The transition of the mobile grating 10 from the first position 2 to the second position 3 defines a movement of the mobile grating 10 which is nonparallel to the grating structures 10a. In an exemplary embodiment, the movement direction of the mobile grating 10 is perpendicular to the optical path 6.

The X-rays start from the radiation source 17. Then they pass the immobile gratings 18 and the mobile grating 10. The X-ray then may be converted to visible light by the scintillator 20a. The converted visible light is then detected by the photodiode array 20. The detector 19 reads out the photodiode array 20 completely at least four times during the movement of the mobile grating 10 between the first position 2 and the second position 3. In an exemplary embodiment, the detector 19 reads out the photodiode array 20 at least four to sixteen, preferably eight, times. The position of the mobile grating 10 between the first position 2 and the second position 3 is known due to the known movement variables, i.e. the amount of the dampening, the strength of the force of the restoring element 12, i.e. the modulus of resilience of the restoring element 12, and the mass of the mobile grating 10. In another exemplary embodiment, a decoder 11a determines the position of the mobile grating 10 along the guiding element 11. The decoder 11a may trigger the detector 19 to read out the photodiode array 20. The decoder 11a may trigger the detector 19 at at least four predetermined positions 29-34 shown in FIG. 4a of the mobile grating 10 while the mobile grating 10 moves from the first position 2 to the second position 3. Therefore, the phase-contrast image may be determined by the readout of the photodiode array 20.

A processing unit 22 may control the locking element 13, the displacing unit 15, and the detector 19. The processing unit 22 therefore provides a signal for the displacement unit 15 to displace the mobile grating 10 from the second position 3 to the first position 2. Furthermore, the processing unit 22 may provide a signal to the locking element 13 such that the locking element 13 will lock the mobile grating 10 in the first position 2. The processing unit may further provide a signal to the locking element 13 to unlock the locking element 13 such that the mobile grating 10 is released from the locking element 13 and may move from the first position 2 to the second position 3. Furthermore, the processing unit 22 may provide a signal to the detector 19 to start the read out of the photodiode array 20.

Figure 5:
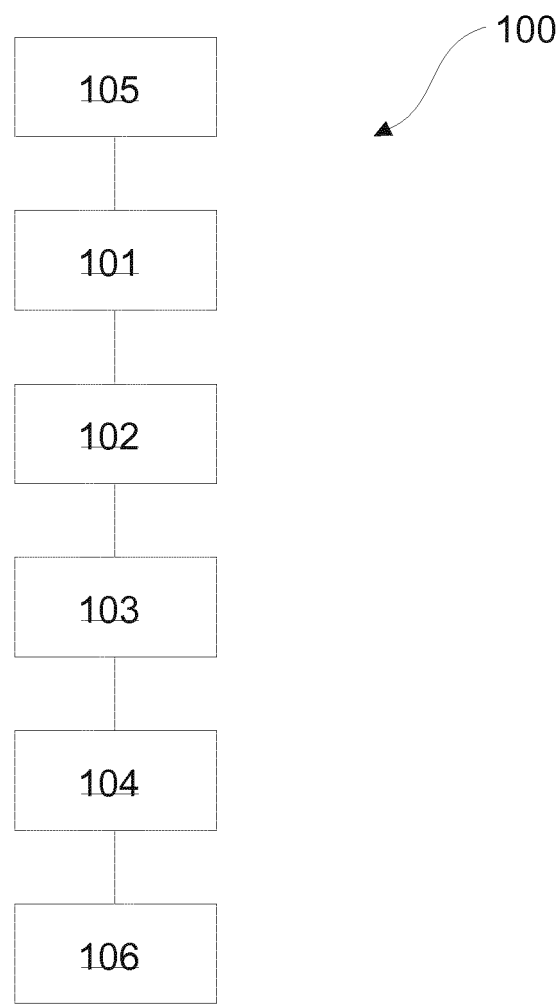
FIG. 5 shows a schematic flow chart of the method.

FIG. 5 shows a flow chart of the method 100 for phase stepping in phase contrast image acquisition.

The method 100 starts with moving 105 the mobile grating into the first position with the displacement unit. The displacement unit 15 displaces the mobile grating 10 from the second position 3 to the first position 2 when the mobile grating 10 has stopped in the second position 3. The beginning of the displacement of the mobile grating 10 by the displacement unit 15 is shown in FIG. 1d. The displacement unit 15 may apply a stronger force to the mobile grating 10 as the restoring element 12 wherein the force of the displacement unit 15 is directed opposite to the force of the restoring element 12. After the displacement unit 15 has brought to the mobile grating 10 into the first position 2, the locking element 13 will lock the mobile grating 10 in the first position 2. After the locking element 13 locks the mobile grating, the displacement unit 15 stops applying force to the mobile grating 10. In an exemplary embodiment, the displacement unit 15 may be detached from the mobile grating 10.

Then a mobile grating is locked 101 in the first position with the locking element, wherein the mobile grating is movable between the first position in the second position. Locking element 13 is configured to lock the position of the mobile grating 10 in the first position 2. This means that if the mobile grating 10 is in the first position 2, the locking element 13 may be actuated such that the mobile grating 10 cannot leave the first position 2, anymore. In this state, the restoring element 12 may still apply a force on the mobile grating 10 which is directed from the first position 2 to the second position 3. However, since the locking element 13 locks the mobile grating 10 in the first position 2, the mobile grating 10 will not move when being locked by the locking element 13.

The locking element 13 is configured to apply a releasable lock on the mobile grating 10. This means that the locking element 13 may be unlocked such that the mobile grating 10 is released from the locking element 13. If the locking element 13 releases the mobile grating 10, the force being applied by the restoring element 12 to the mobile grating 10 will move the mobile grating 10 from the first position 2 to the second position 3.

The locking element 13 is connected to an element which is immobile relative to the mobile grating 10. According to FIGS. 1a-d this may be element 26. If the mobile grating 10 comes into the first position 2, the locking element 13 may connect to the mobile grating 10 in a clamping or form fit manner. The locking element 13 may e.g. comprise a pin which may connect to a corresponding recess on the mobile grating 10. In another exemplary embodiment, the locking element may comprise an electromagnet, wherein the mobile grating may comprise a permanent magnet. The locking is performed if the electromagnet is switched on and if the electromagnet and the permanent magnet are arranged next to each other.

In another exemplary embodiment (not shown), the locking element 13 may be arranged on the guiding element 11. In this case, the locking element 13 is rigidly connected to the guiding element 11 such that the locking element 13 does not move relative to the guiding element 11. The locking element 13 may then for example clamp the mobile grating 10. In another example, the locking element 13 may block the movement of the mobile grating 10 in a form-fit manner, e.g. the locking element 13 may block the mobile grating 10 on the guiding element 11.

In step 102, a force on the mobile grating is applied with the restoring element, wherein the forces directed from the first position to the second position. The restoring element 12 is attached to the mobile grating 10. The restoring element 12 may comprise a connection to an element 26 being immobile in relation to the mobile grating 10. In an exemplary embodiment, the restoring element 12 may be a mechanical spring. In another exemplary embodiment, the restoring element 12 may be an electrical or electromagnetic oscillating element or in a further exemplary embodiment a hydraulic oscillating element. The restoring element 12 applies a force to the mobile grating 10 when the mobile grating 10 is in the first position 2. The force which the restoring element 12 applies to the mobile grating 10 in the first position 2 is directed such, that the mobile grating 10 is moved into the second position 3.

In the second position 3, the restoring element 12 does not apply a force on the mobile grating 10. The force of restoring element 12 in the second position 3 is therefore zero. The force of the restoring element 12 on the mobile grating 10 decreases between the first position 2 and the second position 3. Thus, the restoring element 12 applies a restoring force to the mobile grating 10 if the mobile grating 10 is removed from the second position 3. Furthermore, the mobile grating 10 and the restoring element 12 define a free oscillating system. The only force which moves the mobile grating 10 results from the restoring element 12.

The distance between the first position 2 and the second position 3 spans at least the pitch of the mobile grating 10. Particularly, the distance may be several times this length. This enables covering at least the entire angular span from 0 to 2*Pi for the phase stepping.

The force being applied in step 102 may already be applied when bringing the mobile grating into the first position and locking the mobile grating in the first position.

In step 103, the locking element is unlocked such that the force of the restoring element 12 moves the mobile grating 10 into the second position.

In step 104, the movement of the mobile grating from the first position and the second position is damped with a dampening element. The dampening element 14 dampens the movement of the mobile grating 10 when moving along the guiding element 11. Thus, the combination of the mobile grating 10, the restoring element 12 and the dampening element 14 define a damped oscillating system. In an exemplary embodiment, the dampening element 14 may provide a force on the mobile grating 10 which is directed opposite to the force being applied by the restoring element 12 as shown in FIGS. 1a-d. In an example, the dampening element 14 may be integrated into the restoring element 12. In another exemplary embodiment, the dampening element 14 provides a friction force to the mobile grating 10 when the mobile grating 10 moves along the guiding element 11. Two further exemplary embodiments of the guiding element 11 are shown in FIGS. 2a and 2b.

In another exemplary embodiment (not shown), the dampening element 14 may be a permanent or electro magnet and the mobile grating may comprise a conductor or vice versa. The dampening then results from relative movement of the conductor and the magnet, since eddy currents are induced in the conductor.

The dampening being provided by the dampening element 14 may be chosen such that the phase sampling may be performed as smooth and uniform as possible.

FIG. 2a shows a guiding element 11 being formed out as a guide rail. The dampening element 14 is positioned on the bottom of the guiding element 11. While gliding along the guide rail, the mobile grating 10 may contact the dampening element 14 which applies a friction force on the mobile grating 10.

In FIG. 2b, the dampening element 14 is positioned on an inner lateral side of the guiding element 11 which comes into contact with the mobile grating 10. While the mobile grating 10 moves along the guide rail, the dampening element 14 applies a force being directed opposite to the force being applied by the restoring element 12.

Concerning the damped oscillation of the mobile grating 10, if the dampening provided by the dampening element 14 is zero, the movement of the mobile grating 10 will be a free oscillation.

A diagram showing the movement of a free oscillating mobile grating 10 is shown in FIG. 4a. The movement of the mobile grating 10 in this case follows a cosine function 27. The starting point of the cosine function is at the first position 2. The movement of the mobile grating 10 then transfers the mobile grating 10 to the second position 3 and further into a third position 4.

A phase stepped measurement for the phase-contrast image acquisition may be applied in the linear portion of the cosine function 27 being indicated by the bars 29 to 34. In this portion, the cosine function 27 is close to a linear function.

The dampening being provided by the dampening element 14 may further be under dampening, critical dampening or over dampening. In the free oscillating and in the under dampening case, the movement of the mobile grating 10 will transfer from the first position 2 to the second position 3 and then further towards or in direction of the third position 4 being shown in FIG. 1c. In the third position 4, the restoring element 12 applies a force to the mobile grating 10 which is directed to the second position 3. The mobile grating 10 will therefore oscillate around the second position 3. In the under dampening case, the distance which the mobile grating 10 moves from the second position 3 will decrease with every passing of the second position 3 until the mobile grating 10 will stop its movement in the second position 3.

In the critically dampened case, the mobile grating 10 will move from the first position 2 to the second position 3 and then stay in the second position 3. This means, that the mobile grating 10 will slow down on the way to the second position 3 and then stop when reaching the second position 3.

In the over damped case, the mobile grating will move slower than in the critically damped case from the first position 2 to the second position 3 and then stop in the second position 3.

An example of a critically damped case or an over damped case is shown in FIG. 4b. The movement path 28 starts at the first position 2 and then transfers towards the second position 3. When approaching the second position 3, the movement of the mobile grating 10 until it stops when the mobile grating 10 reaches the second position 3.

In step 106, a detector 19 being arranged on an end of an optical path extending to the mobile grating why the mobile grating moves between the first position and the second position is read out at least four times. The detector 19 may comprise a scintillator 20a and a photodiode array 20. The scintillator 20a converts X-ray radiation to visible light which may be detected by the photodiode array 20. Thus, detector 19 reads out the photodiode array 20 completely at least four times while the mobile grating 10 moves from the first position 2 to the second position 3. In an exemplary embodiment, the detector 19 reads out the photodiode array 20 at least four to sixteen, preferably eight, times. In one exemplary embodiment, the position of the mobile grating 10 between the first position 2 and the second position 3 is known due to the known movement variables, i.e. the amount of the dampening, the strength of the force of the restoring element 12, i.e. the modulus of resilience of the restoring element 12, and the mass of the mobile grating 10. In another exemplary embodiment, a decoder 11a determines the position of the mobile grating 10 along the guiding element 11. The decoder 11a may trigger the detector 19 to read out the photodiode array 20. The decoder 11a may trigger the detector 19 at least four predetermined positions of the mobile grating 10 while the mobile grating 10 moves from the first position 2 to the second position 3. Therefore, the phase-contrast image may be determined by the readout of the photodiode array 20.

A processing unit 22 may control the locking element 13, the displacing unit 15, and the detector 19. The processing unit 22 therefore provides a signal for the displacement unit 15 to displace the mobile grating 10 from the second position 3 to the first position 2. Furthermore, the processing unit 22 may provide a signal to the locking element 13 such that the locking element 13 will lock the mobile grating 10 in the first position 2. The processing unit may further provide a signal to the locking element 13 to unlock the locking element 13 such that the mobile grating 10 is released from the locking element 13 and may move from the first position 2 to the second position 3. Furthermore, the processing unit 22 may provide a signal to the detector 19 to start the read out of the photodiode array 20.

In another exemplary embodiment of the present invention, a computer program or a computer program element 21 is provided that is characterized by being adapted to execute the method steps of the method according to one of the preceding embodiments, on an appropriate system.

The computer program element 21 might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium 23, such as a CD-ROM, is presented wherein the computer readable medium 23 has a computer program element 21 stored on it which computer program element 21 is described by the preceding section. A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element 21 available for downloading is provided, which computer program element 21 is arranged to perform a method according to one of the previously described embodiments of the invention.

It should be noted that embodiments of the invention are described regarding different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for phase stepping in phase contrast image acquisition, the device comprising:
 a phase contrast image acquisition apparatus including a radiation source; and
 a device comprising:
  a mobile grating spaced apart, in an optical axis direction of a radiation emitted from the radiation source, from the radiation source, wherein the mobile grating is movable along a linear direction different from the optical axis direction;
  a guide,
  wherein when the mobile grating is moving along the linear direction different from the optical axis direction, the guide is configured to guide the mobile grating between a first position and a second position and along the linear direction different from the optical axis direction, and
  wherein the first position is offset from the second position in the linear direction different from the optical axis direction;
  a restorer configured to apply a force to the mobile grating, the force being directed from the first position to the second position; and
 a lock configured to releasably lock the mobile grating in the first position.

2. The system according to claim 1, wherein the device further comprises:
 a position decoder configured to detect a position of the mobile grating along the guide and emit a trigger signal for a detector if the mobile grating passes predefined positions along the guiding element guide.

3. The system according to claim 1, wherein the mobile grating is configured to perform a continuous movement between the first position and the second position.

4. The system according to claim 1, wherein the device further comprises:
 a movement dampener configured to dampen a movement of the mobile grating between the first position and the second position.

5. The system according to claim 4, wherein the movement dampener is controllable.

6. The system according to claim 4, wherein the movement dampener applies at least an under critical dampening to the movement of the mobile grating.

7. The system according to claim 1, wherein the device further comprises:
 a mobile grating mover configured to move the mobile grating into the first position.

8. The system according to claim 1,
 wherein the phase contrast image acquisition apparatus comprises
  at least one immobile grating; and
 wherein a movement of the mobile grating from the first position to the second position shifts the mobile grating relative to the at least one immobile grating.

9. The system according to claim 1, wherein the phase contrast image acquisition apparatus comprises:
 a detector that includes
  a photodiode array; and
  a scintillator;
 wherein the photodiode array matches the scintillator; and
 wherein the detector is configured to completely read out the photodiode array at least four times during a movement of the mobile grating between the first position and the second position.

10. A method for phase stepping in phase contrast image acquisition, the method comprising:

locking a mobile grating in a first position with a lock,
wherein the mobile grating and a radiation source are spaced apart from each other in an optical axis direction of a radiation emitted from the radiation source,
wherein the mobile grating is movable between the first position and a second position and along a linear direction different from the optical axis direction of the radiation, and
wherein the first position is offset from the second position in the linear direction different from the optical axis direction;
applying a force on the mobile grating with a restorer, wherein the force is directed from the first position to the second position; and
unlocking the lock such that the force moves the mobile grating into the second position.

11. The method according to claim 10, further comprising:
reading out a detector on which X-ray radiation passing the mobile grating falls on.

* * * * *